(12) United States Patent
Hadjicostis

(10) Patent No.: US 8,414,492 B2
(45) Date of Patent: *Apr. 9, 2013

(54) IMAGE GUIDED INTRACARDIAC CATHETERS

(75) Inventor: Andreas Hadjicostis, Carmel, IN (US)

(73) Assignee: Meridian Cardiovascular Systems, Inc., Carmel, IN (US)

(*) Notice: Subject to any disclaimer, the term of this patent is extended or adjusted under 35 U.S.C. 154(b) by 406 days.

This patent is subject to a terminal disclaimer.

(21) Appl. No.: 12/509,880

(22) Filed: Jul. 27, 2009

(65) Prior Publication Data

US 2009/0287090 A1    Nov. 19, 2009

Related U.S. Application Data

(63) Continuation of application No. PCT/US2008/071283, filed on Jul. 27, 2008.

(60) Provisional application No. 60/962,160, filed on Jul. 27, 2007.

(51) Int. Cl.
*A61B 8/00* (2006.01)

(52) U.S. Cl.
USPC .......................................................... 600/439

(58) Field of Classification Search .................. 600/374, 600/424, 439, 471
See application file for complete search history.

(56) References Cited

U.S. PATENT DOCUMENTS

| | | | | |
|---|---|---|---|---|
| 5,687,737 A * | 11/1997 | Branham et al. | ............... | 600/523 |
| 5,840,031 A * | 11/1998 | Crowley | ........................ | 600/440 |
| 5,842,994 A * | 12/1998 | TenHoff et al. | ............... | 600/466 |
| 6,066,096 A | 5/2000 | Smith | | |
| 6,572,551 B1 * | 6/2003 | Smith et al. | .................... | 600/459 |
| 2002/0026118 A1 | 2/2002 | Govari | | |
| 2004/0147920 A1 * | 7/2004 | Keidar | ............................ | 606/34 |
| 2004/0193032 A1 * | 9/2004 | Mogul | ............................ | 600/374 |
| 2005/0203410 A1 | 9/2005 | Jenkins | | |

OTHER PUBLICATIONS

International Search Report from PCT/US20087/0718283.
U.S. Appl. No. 12/509,902, filed Jul. 27, 2009 entitled Intracardiac Catheters with Image Field Electrodes.
Written Opinion from PCT/US2008/071283.

* cited by examiner

*Primary Examiner* — Jonathan Cwern
(74) *Attorney, Agent, or Firm* — Timothy E Siegel Patent Law, PLLC

(57) ABSTRACT

An intracardiac catheter for ultrasound guided ablation and EP mapping. Ablation and mapping electrodes 34, 36, 38, 39 are carried on the surface of an outer catheter 30 and an ultrasound array is mounted inside an inner catheter 20. Backloading the inner catheter into the outer catheter provides the ultrasound array in position to image tissue near the surface electrodes. An acoustic coupling fluid is provided between the catheters and a number of the electrodes 34, 38 are positioned directly within the image field of the array.

16 Claims, 5 Drawing Sheets

IMAGE GUIDED INTRACARDIAC CATHETERS

RELATED APPLICATION DATA

This application is a continuation of PCT/US2008/71283 filed Jul. 27, 2008 which claims the benefit of U.S. Provisional Application No. 60/962,160 filed Jul. 27, 2007, the disclosures of which are incorporated by reference.

TECHNICAL FIELD

This application relates to ultrasonic imaging catheters for diagnostic and/or therapeutic use and methods of making the same. More particularly, but not exclusively, the application relates to intracardiac catheters having surface electrodes and an ultrasound imaging array for providing guided tissue ablation and/or guided electrophysiological mapping capabilities.

BACKGROUND

The action of the human heart is controlled by propagation of electrical activity in various regions of the heart. The presence of abnormal accessory pathways in the heart can lead to conditions such as ventricular tachycardia and atrial flutter.

Physicians have found that they can detect malfunctions of the heart by probing the heart with a catheter fitted with one or more electrodes and having steering capability, measuring voltages within the heart, and observing the waveforms. Once a physician understands how the electrical activity of the heart is operating he can, if he wishes to do so, choose to "disconnect" certain portions of the heart electrically by the process of ablation.

The electrical activity of the heart is detected and read in accordance with a mapping procedure to determine the presence of abnormal accessory pathways in the heart. A typical mapping procedure involves using electrophysiology sensing electrodes mounted on a catheter as remote controlled voltage testing probes to test various locations in the heart. This mapping is known as electrophysiology (EP) testing and can be used to diagnose sinus node dysfunction, identify arrhythmias, check impulse generation or conduction in the atria and ventricles, or investigate the need for pacemakers or implantable cardiac defibrillator.

Ablation is sometimes performed as a part of the EP test to destroy small amounts of heart tissue that are interfering with electrical impulses, or causing arrhythmias. The process of ablation is a destructive process in which a portion of a catheter (typically the tip) is used to apply a short burst of RF energy to the heart tissue to burn a certain section of the heart, which stops the propagation of an electrical signal from one portion of the heart to another.

Existing EP catheters are typically positioned at various positions in the heart under fluoroscopic guidance. The x-rays show the catheter, and can also show the heart itself and thus the position of the catheter relative to the heart (if dye injections are made). The clinician tries to visualize the position of the catheter in the heart in the various chambers. Electrical means are used to determine whether or not the electrode is in contact with the heart, and this information is collected in a computer and/or shown on an EKG display. During the course of a typical procedure the operator will frequently return to one or more positions, and will look for particular waveforms that he sees from the sensing electrodes to determine whether the catheter has returned to the desired position. Particular methods of mapping include activation sequence mapping, voltage amplitude mapping, pacing morphology mapping, and entrainment mapping. Typically, more than one catheter is used in a given procedure, and the catheters are constructed with steering or torquing devices that assist in positioning of the catheters within the heart.

Unfortunately, the use of fluoroscopy for ascertaining the catheter position does not provide adequate detail in real time and also exposes the patient and health professionals to undesirable ionizing radiation. Other visualization technologies, such as electromagnetic mapping of the catheter location, are expensive and also lack desirable accuracy.

The present application is directed to the use of high frequency ultrasound visualization during EP procedures and provides, in one particular form, a novel catheter for use in EP procedures which can produce high resolution, real time ultrasound images that are coincident with the location of the electrodes so as to provide unambiguous visual feedback to the operator. Novel catheter designs and methods of construction are also disclosed for producing ultrasound imaging catheters for these and other diagnostic and/or therapeutic applications.

SUMMARY

The present invention provides systems and techniques for constructing and using a catheter which incorporates an ultrasound imaging array and one or more surface electrodes for providing guided therapy or diagnostics in a patient. While the actual nature of the invention covered herein can only be determined with reference to the claims appended hereto, certain aspects of the invention that are characteristic of the embodiments disclosed herein are described briefly as follows.

According to one aspect, an ultrasonic imaging catheter is constructed by providing an inner catheter and an outer catheter, wherein the inner catheter contains a high frequency imaging array and the outer catheter includes surface electrodes. During assembly, the inner catheter is back loaded into a lumen of the outer catheter, and an acoustic coupling fluid is provided in the lumen of the outer catheter to assure an acoustic path for the high frequency ultrasound to image tissue near the surface electrodes. The outer catheter may be configured to contain all of the electrical connections and wiring for the surface electrodes along with steering capabilities, and the inner catheter may be configured to contain all of the array and associated wiring and connections, which simplifies manufacture and assembly.

According to another aspect, a steerable intracardiac catheter is provided which combines high quality ultrasonic imaging capabilities with a number of ablation and/or mapping electrodes wherein some of the electrodes are positioned directly in the image field of the array. The array is configured to transmit and receive high frequency ultrasound through and/or around the electrodes so as to provide highly relevant visualization information of the tissue being treated. Electrodes positioned in the image field may be thin electrodes so as to be substantially transparent to the high frequency ultrasound. In a variation, a thick electrode may be positioned in the image field to block the transmission of ultrasound so as to effectively segment the array into first and second sub apertures on either side of the thick electrode, which can serve to increase the lateral resolution of the overall imaging array.

These and other aspects are discussed below

BRIEF DESCRIPTION OF THE FIGURES

Although the characteristic features of this invention will be particularly pointed out in the claims, the invention itself, and the manner in which it may be made and used, may be better understood by referring to the following description taken in connection with the accompanying figures forming a part thereof but which are not drawn to scale.

DETAILED DESCRIPTION

Figure 1:
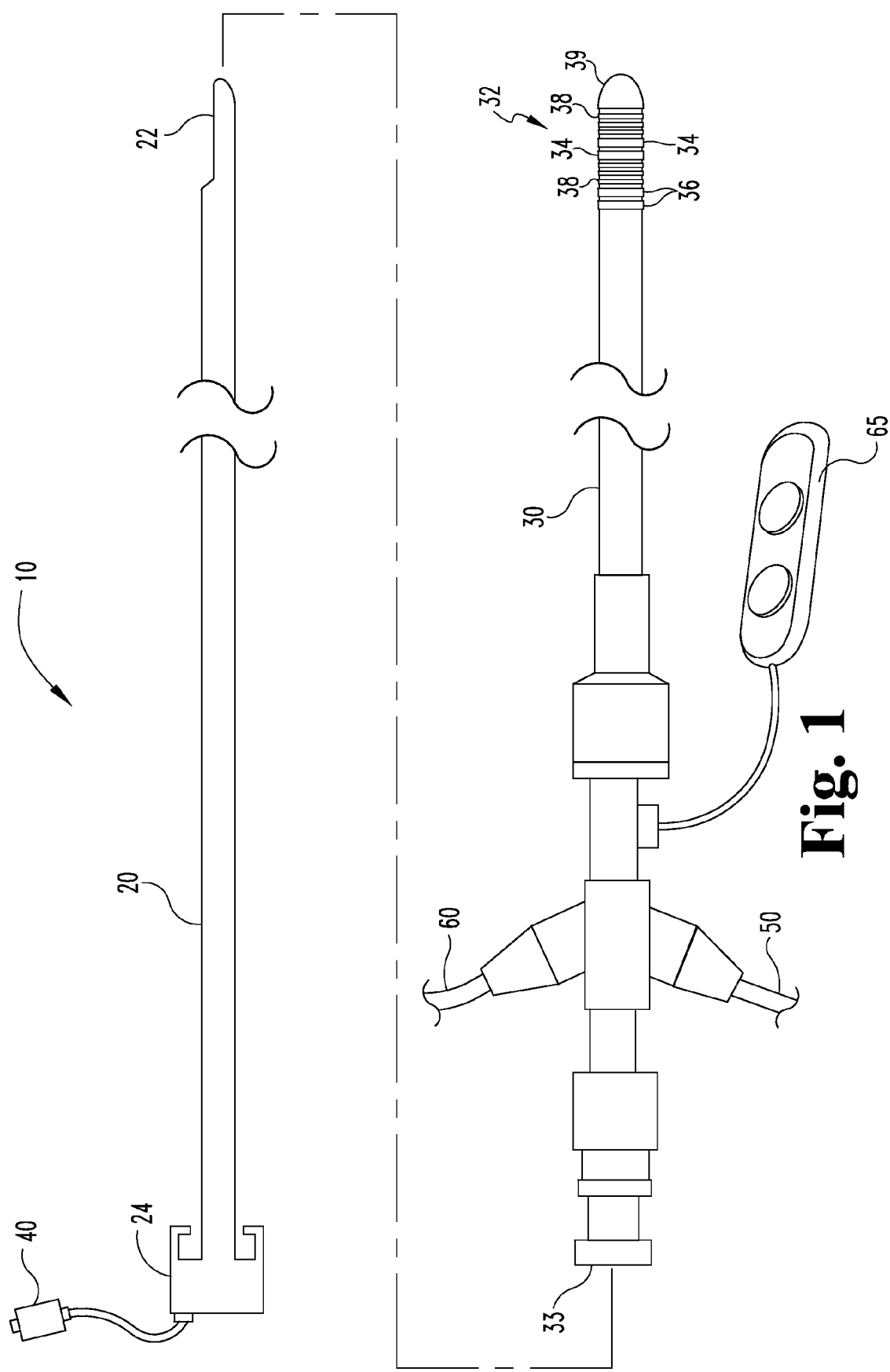
FIG. 1 is an assembly view illustrating the inner and outer catheters of an intracardiac catheter according to one embodiment.

For the purposes of promoting an understanding of the principles of the invention, reference will now be made to the embodiments illustrated in the drawings and specific language will be used to describe the same. It will nevertheless be understood that no limitation of the scope of the invention is hereby intended. Alterations and further modifications in the illustrated devices, and such further applications of the principles of the invention as illustrated herein are contemplated as would normally occur to one skilled in the art to which the invention relates.

Figure 3:
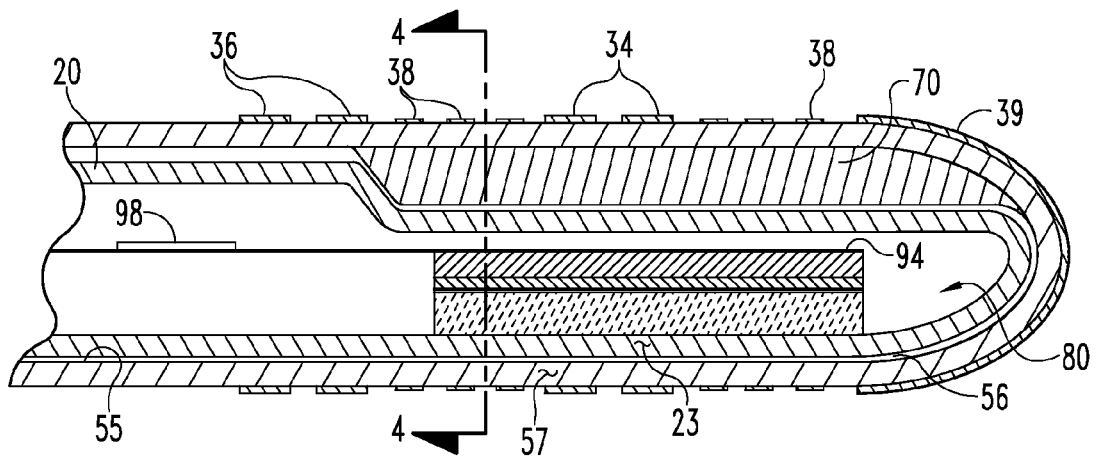
FIG. 3 is a side cross sectional view of the distal end of the assembled catheter of FIG. 1.
Figure 4:
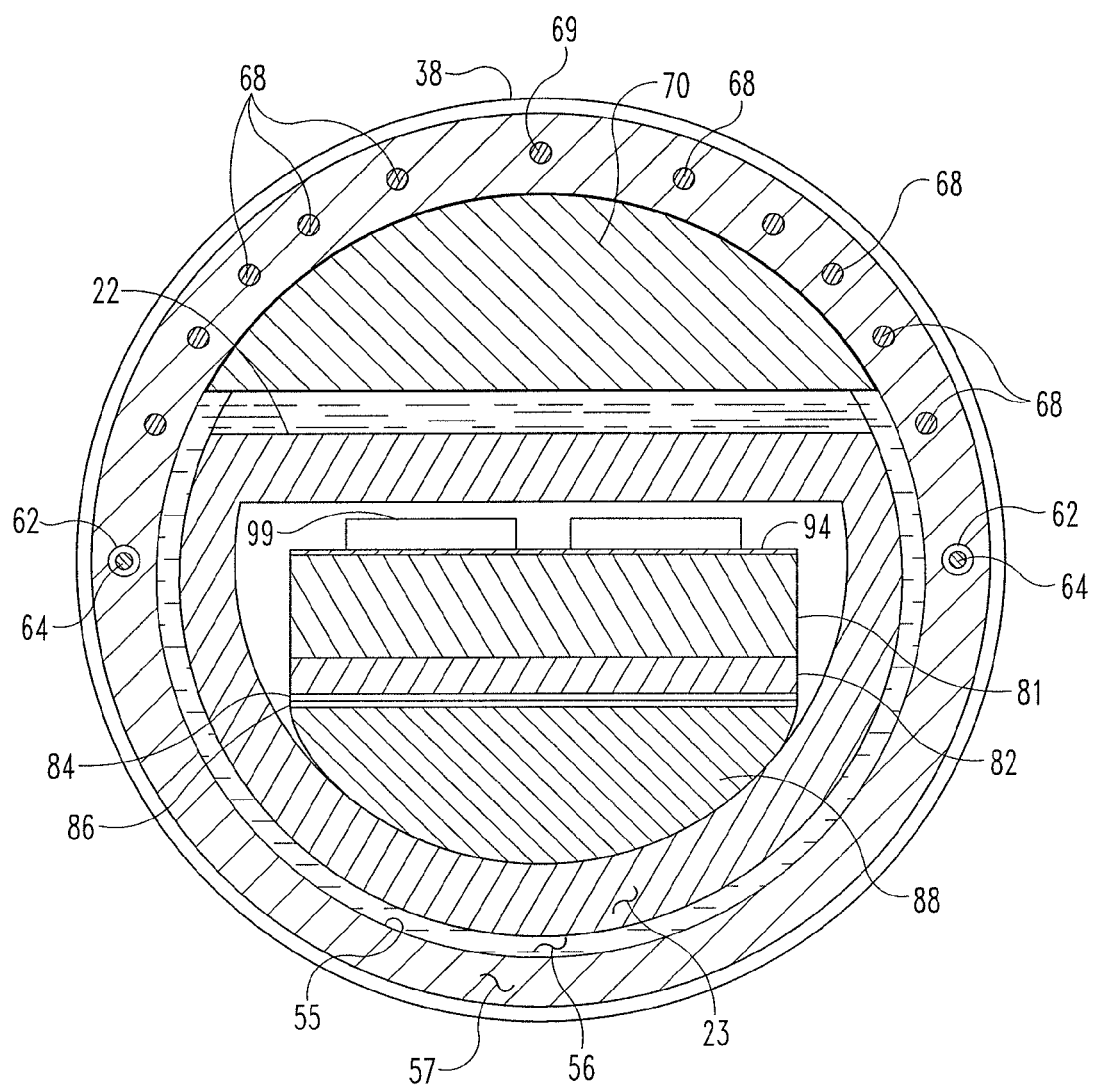
FIG. 4 is an end cross sectional view of the distal end of the assembled catheter as indicated in FIG. 3.

In one form, the present invention provides an intracardiac catheter adapted to provide real time ultrasound visualization during an EP procedure. With reference to FIGS. 1-4, intracardiac catheter 10 is constructed by back loading an inner catheter 20 into an outer catheter 30. The outer catheter 30 includes a distal portion 32 containing a number of surface electrodes 34, 36, 38, 39, and these surface electrodes are adapted to carry out electrical mapping and/or ablation techniques inside the heart. The surface electrodes are positioned on the outer surface of catheter 30 and are electrically connected to connector 50 or connector 60 via wires 68 (FIG. 4). Wires 68 are embedded in wall 57 of catheter 30, which may be achieved via an extrusion process. Alternatively, wires 68 may be bundled and routed through a common lumen of catheter 30.

Connectors 50 and 60 serve to couple the surface electrodes to appropriate equipment (not shown) for performing ablation and/or electrical mapping with the surface electrodes. For example, connector 50 may couple certain ones of the electrodes (e.g. 34, 36, 38, 39) to an RF generator (not shown) while connector 60 couples other ones of the electrodes (e.g. 38) to EP mapping equipment (not shown). In one implementation, each surface electrode 34, 36, 38 is connected to a respective set of conductive wires 68 to permit independent operation and control of the various surface electrodes. Electrode temperatures can be sensed by thermocouples (not shown) connected to the relevant control system via embedded wire 69.

Outer catheter 30 includes a steering mechanism 65 coupled to steering wires 64, which are disposed in corresponding lumens 62 and run through the distal portion 32. The steering mechanism 65 allows the operator to articulate tip 32 during use.

Inner catheter 20 includes an ultrasound transducer imaging array 80 and is designed to be back loaded into lumen 55 of outer catheter 30 via proximal port 33, as depicted in FIG. 1. When assembled, proximal coupling 24 on inner catheter 20 engages with proximal port 33 of outer catheter 30 and array 80 is located in distal tip 32 as shown in FIG. 3. Cabling from array 80 extends through the catheter 20 and terminates in a multi pin connector 40 for coupling to an ultrasound system (not shown).

The distal section 22 of catheter 20 is flattened into a truncated circle (i.e. D shaped cross section) to accommodate a radiopaque marker 70, which is integrated into lumen 55 to facilitate x-ray visualization. The non-circular cross sections of distal section 22 of catheter 20 and lumen 55 serves to establish and maintain a common angular orientation between the catheters 20, 30.

Array 80 is configured as a side looking array and serves to image the tissue adjacent one or more of the surface electrodes. The array transmits and receives ultrasound pulses which travel through the catheter walls 23 and 57 and into the surrounding tissue. An acoustic coupling fluid 56 is preferably provided between the inner and outer catheters 20, 30 and serves to facilitate energy transmission and minimize interference or scattering of the ultrasound due to the wall transitions. A suitable fluid 56 may be a saline solution or other biocompatible liquids or gels.

Fluid 56 may be injected into port 33 and/or applied to catheter 20 prior to introduction of catheter 20, in which case fluid 56 may also function as a lubricant to facilitate catheter 20 sliding into position. Alternatively or in addition, fluid 56 may be injected into the void space between walls 23, 57 after assembly. Proximal fitting 24 may be designed to create a fluid tight connection with port 33 to prevent loss of the acoustic coupling fluid 56 during use. To assure a more permanent connection between the catheters 20, 30, glue or adhesives may be used in place of or in addition to fitting 24.

Ultrasound array 80 is a multi-element transducer array which operates at relatively high frequency, for example in the range of about 7.5-15 MHz. In one form, array 80 comprises a linear or one-dimensional array or a multi-dimensional array. As illustrated, array 80 comprises a diced array of piezoelectric elements 82 mounted on a flex circuit 94. Suitable flex circuits and useful techniques for constructing and mounting piezoelectric arrays on flex circuits are described in, for example, U.S. Pat. No. 7,226,417 to Eberle and US 2004/0254471 to Hadjicostis et al. However, the catheter 10 may be usefully implemented with a number of different imaging arrays known in the art, for example those described in U.S. Pat. Nos. 5,857,974 and 6,962,567 to Eberle et al., U.S. Pat. No. 6,994,674 to Shelgaskow et al., and/or U.S. Pat. No. 7,156,812 to Seward et al.

Figure 2:
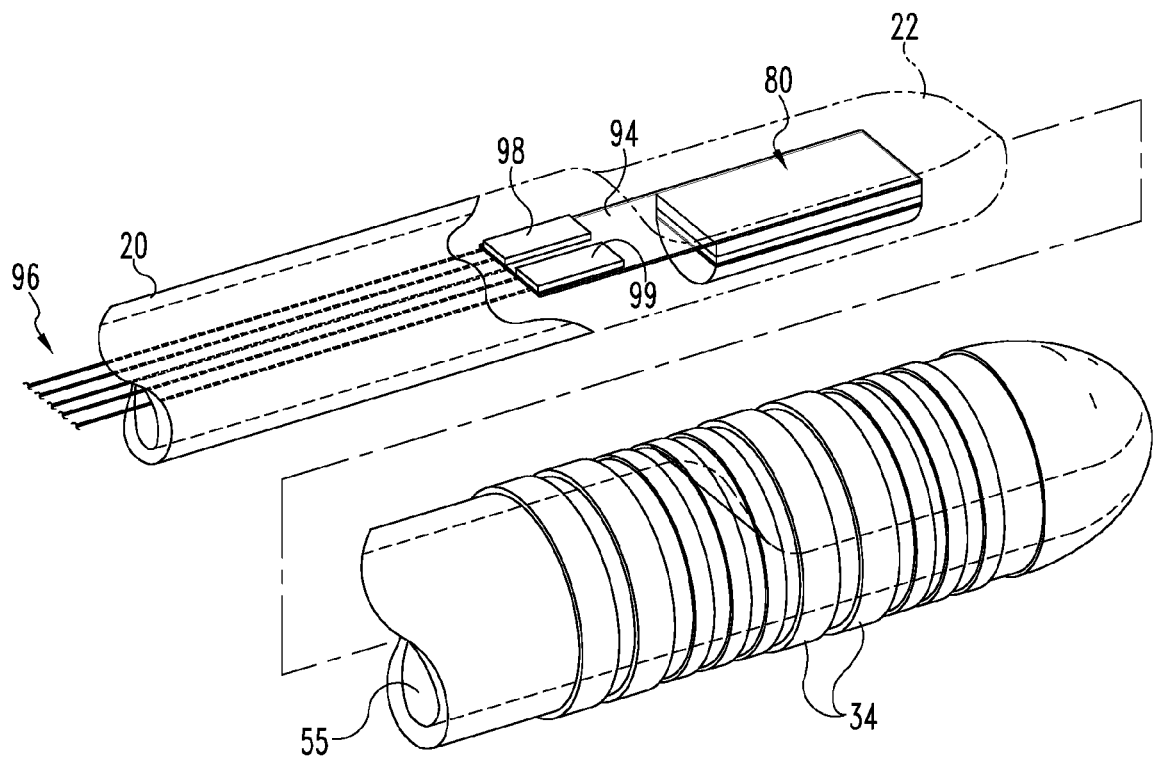
FIG. 2 is an enlarged view of the distal ends of the inner and outer catheters of FIG. 1.
Figure 5:
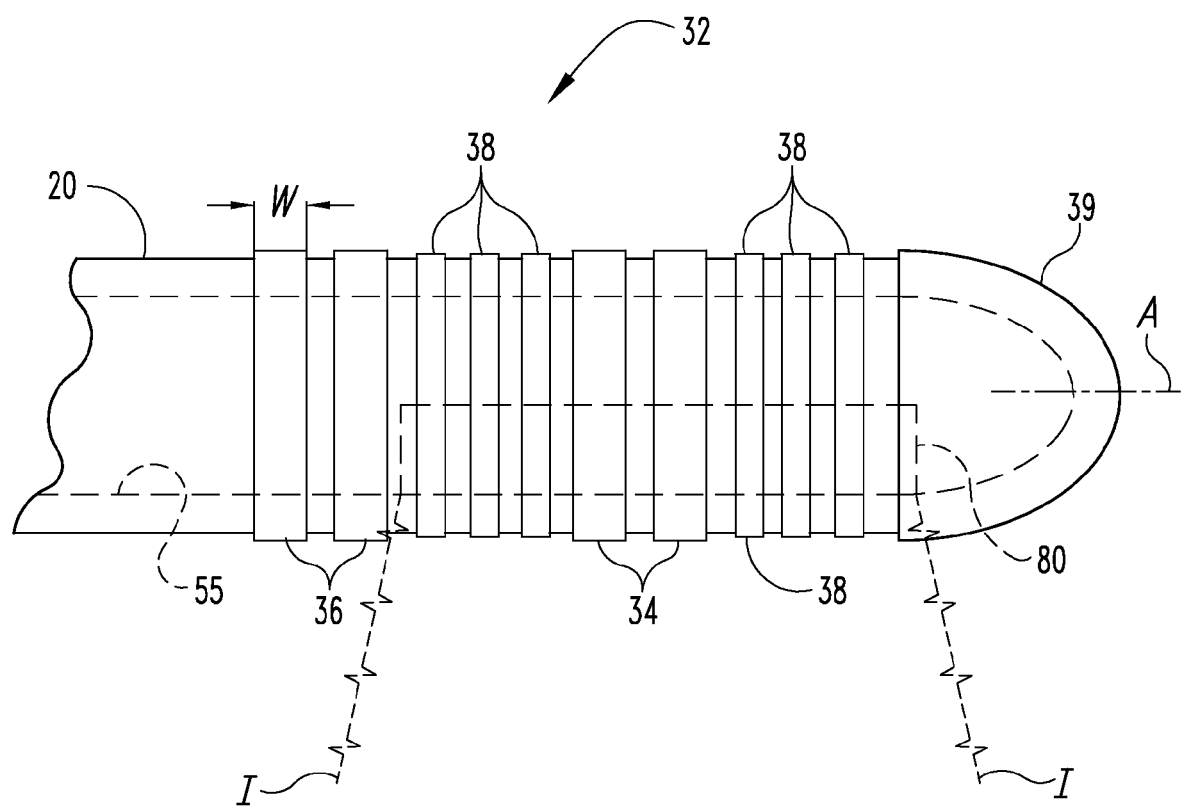
FIG. 5 is a side schematic of the distal end showing the relative location of the ultrasound array and various surface electrodes in connection with a second embodiment wherein the array is directly bonded to the outer catheter.

With reference to FIGS. 2 and 4, array 80 includes a layer of diced piezoelectric elements 82, an acoustic backing layer 81, and one or more acoustic matching layers 84, 86. A lens piece 88 is mounted to the last matching layer and provides an outer curved surface that conforms with and may be bonded to the curved wall 23 of inner catheter 20. It is also contemplated that array 80 may be mounted directly to the inside of lumen 55, as shown in FIG. 5, or otherwise incorporated into the outer catheter 20.

The elements 82 are formed by dicing a commercially available piezoelectric work piece, for example, CTS 3257HD or CTS 3265HD (CTS Electronic Components, Inc. Albuquerque, N. Mex.). A dicing saw is used to make a series of parallel cuts in a first direction and the resulting kerfs are filled with a suitable epoxy. A metallizing layer is deposited over the distal face of the piezoelectric elements 82 to serve as a common ground electrode. The proximal face of each of the elements 82 is in electrical contact with individual signal lines (not shown), which extend through the acoustic backing layer 81 to a flex circuit 94. The proximal face of each of the elements 82 may include its own metallizing layer (not shown) to facilitate electrical connection with the individual signal lines, and the matching layers 84, 86 are applied to the distal face of the elements 82. Alternatively, elements 82 may be applied directly to the flex circuit 94 and the acoustic backing layer 81 may be applied to the back side of the flex circuit, in which case there is no need for signals lines in the backing layer 81.

The array 80 is mounted to a flexible circuit substrate 94, which comprises a flexible substrate material (e.g. a polyimide film) and metallic interconnection circuitry (not shown). The interconnection circuitry comprises conductor lines deposited upon the surface of the flex circuit 94 which couples the array 82 to one or more integrated circuit chips 98, 99 each of which incorporates appropriate multiplexers, pre-amplifiers and other electrical integrated circuits such as filters, signal conditioners, etc. Ultrasound cabling 96 runs proximally to electrically connect the flex circuit 94 to the connector 40 for an ultrasound imaging system (not shown).

Cabling 96 may comprise a co-axial cable bundle 96 that includes analog signal lines and digital control wires for bidirectional communication with array 80 via flex circuit 94. The cabling 96 may comprise analog miniature co-axial cables (each of which typically has diameter 46-54 AWG). The gauge of the digital control wires may be about 42-50 AWG. The number of analog lines may vary from 16 to 128 with the preferred embodiment being 32 to 64. The digital control lines may typically vary from be 5-20. The multiplexers in the chips 98, 99 allow the ultrasound system to be able to separately address each individual element (if desired) even though the number of analog signal lines in bundle 96 may be substantially less than the number of elements in the array.

The ultrasound system (not shown) may include analog interface circuitry, Digital Signal Processors (DSP), data processors, memory components, input devices, and a display as known in the art. The ultrasound system activates the transducer array 80 to acquire imaging information by any number of techniques known in the art based on the chosen configuration of the array. In typical applications, array 80 would operate as a phased array, and if the number of elements is large the array 80 may be operated via synthetic aperture approach.

As is known in the art, during synthetic aperture imaging, predefined subsets of the elements in the array are activated in sequence and the resulting responses are collected to form a complete image. This approach may be employed for any type of array (e.g. 1-D or multi-dimensional arrays) wherein the number of elements in the array is much greater than the corresponding number of analog signal lines. For example, if there are 32 analogue lines that are used to drive a 324-element array, then the system 40 is configured to transmit and receive with up to 32 elements at a time. The information from one group elements (e.g. the first 32) is collected and stored, and the processes repeats with another group of elements (e.g. the second 32) until all the elements in the array have been addressed. The total information received from all the elements is then processed to produce a single image frame.

In addition to transmitting and receiving with the sub-groups of 32 elements, ultrasound system may also be implemented to transmit with a first sub group of elements and to receive sequentially with every other sub-group of elements. For a 324 element array, there would be ten (10) 32-element sub-groups present with 4 elements not being used. The signals received from all the receiving sub-groups in the array are called "cross products." Collecting the cross products helps to increase overall image quality.

As described previously, the surface electrodes 34, 36, 38, 39 may provide both diagnostic (e.g. EP mapping) and therapeutic (e.g. ablation) functionalities. The relative arrangement of the array 80 with respect to the electrodes can provide a number of benefits. With reference to FIG. 5, array 80 is oriented longitudinally along the axis A of the distal tip and transmits generally orthogonally to the axis A in what is referred to as a "side looking" arrangement. Array 80 is operable to image tissue contained within its image field, the generally boundaries of which are schematically indicated in FIG. 5 with the Is. A number of the surface electrodes, namely electrodes 38 and 34 as well as a portion of electrode 39 are within the bounds of the image field. Those electrodes 38, 34 have the capability of interfering with the ultrasound propagation or otherwise degrading the overall image quality.

In one implementation, such interference by electrodes in the image field can be largely avoided by limiting the thickness of the electrodes, wherein thickness refers to the dimension orthogonal to the direction of ultrasound propagation. Such electrodes may be constructed from a thin layer of gold, titanium, aluminum, magnesium, beryllium or any other metal or metallic material having high electrical conductivity, high sound propagation velocity and/or low density. In one form, the electrodes are metallic strips that are sufficiently thin that the ultrasound passes without substantial attenuation or interference, for example having a thickness less than about 8 micrometers, such as in the range of 0.2 to 8 µm, 0.4 to 6 µm, 0.5 to 4 µm, 0.7 to 2 µm, 0.9 to 1.5 µm, or 1-3 µm. The thin metallic strips may applied by a vapor deposition technique or any other convention process for forming a thin layer of metallic material.

The use of thicker electrodes in the image field is also contemplated. For example, electrodes 34 are positioned near the midpoint of the array 80 and may be used to effectively divide the array 80 into first and second sections (left side and right side of electrodes 34) which effectively become sub-apertures. Ultrasound images may be produced by the combined operation of the two array sub-apertures. The overall aperture of the array will increase by the width of the center electrodes 34, which can serve to improve overall lateral resolution. The thickness of these "opaque" electrodes may be 25-75 µm.

The width W of the various surface electrodes may also be varied, which provides the operator control over treatment size. It is contemplated that electrodes may be 0.25 to 2.5 mm in width W with inter electrode spacing of 0.5 to 5 mm.

Figure 6:
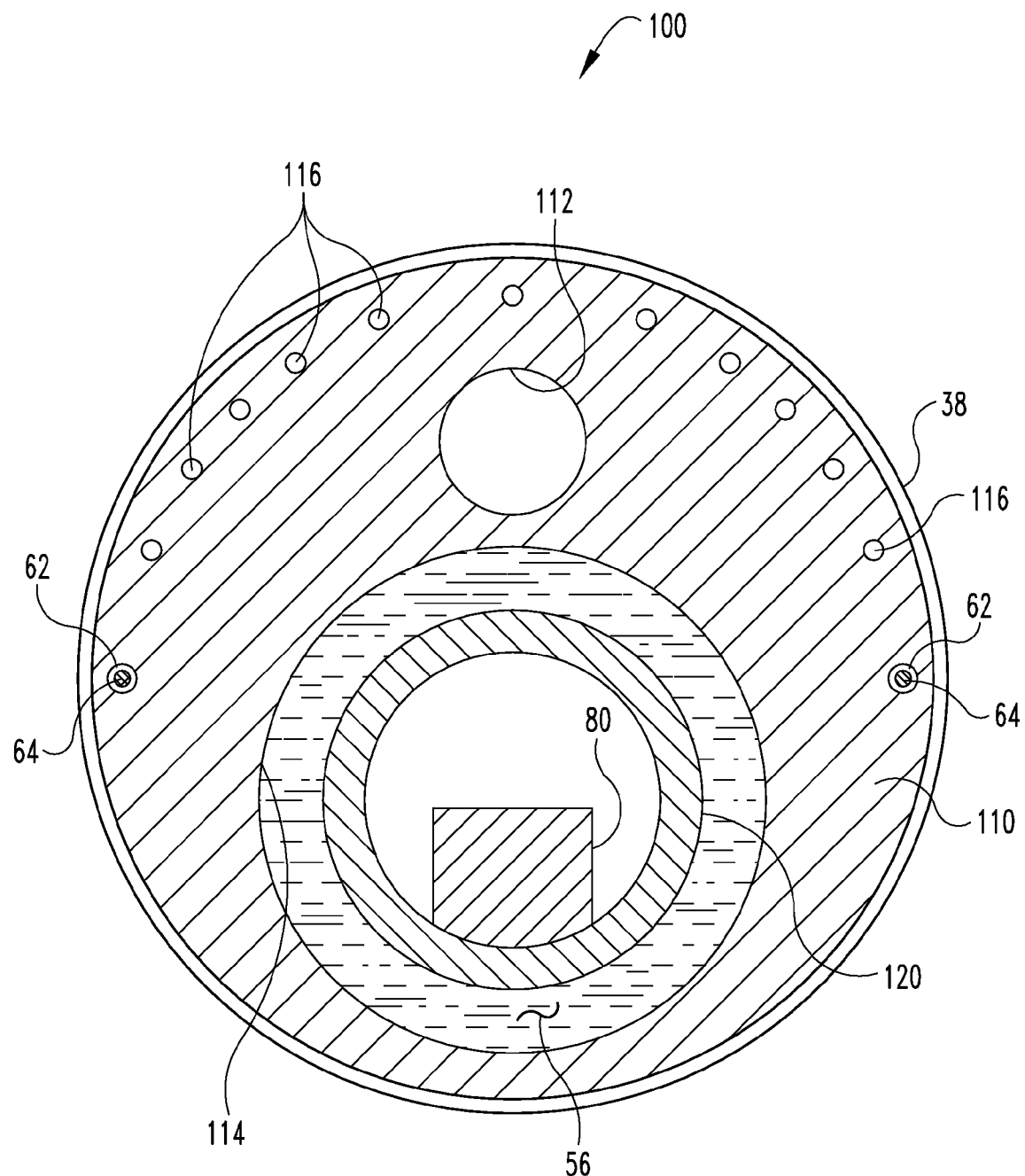
FIG. 6 is an end cross sectional view of the distal end of an assembled catheter according to a further embodiment.

Intracardiac catheters according to the present invention may be designed for introduction into the patient by any conventional means, such as by being introduced via an introducer sheath or by being inserted over a guide wire. FIG. 6 illustrates an alternative configuration for a catheter 100 wherein outer catheter body 110 defines a guide wire lumen 112 and lumen 114 which receives an inner catheter 120 containing ultrasound array 80. As depicted, the cross section of inner catheter 120 is essentially circular such that catheter 120 may be axially rotated in lumen 114. Alternatively, lumen 114 and catheter 120 may have substantially matching non-circular cross sections to substantially prevent rotation. In lieu of embedded electrical wires, outer catheter 110 includes a number of lumens 116, which may receive individual or bundles of wires.

Catheters can be constructed of any useful materials and in a variety of lengths and sizes, for example 4F-10F and 60-150 cm in length. A preferred material for the catheter tip 32 is a high temperature plastic or ceramic, such as Torlon™ plastic or aluminum oxide ceramic. The number of RF transmitting electrodes can vary in number from 2 to 12. The radio-opaque marker 70 may be made from a dense metal material such as tungsten, iridium or other metal having density over 18 gm/cc. The traces on the flex circuit 94 that are connected to the piezoelectric array may have width in the range 5-20 micrometers and thickness 1-3 micrometers. A one dimensional array 80 may have 32 to 96 elements and overall length in the range of 3-8 mm. The frequency bandwidth of the elements may be in the range 50%-120% with an insertion loss less than −20 dB. A useful two dimensional array 80 may have a number of elements in the range of 256-1024

The radius of curvature of the cylindrical lens 88 may be in the range of 5-50 mm, and the array 80 may be bonded to wall 23, which may be in the form of a thin plastic tube (0.002" thickness or less). The preferred operating frequency of the ultrasound array elements is in the range of 7.5-15 MHz. Array 80 may be phased and may have half-wavelength element spacing for optimum ultrasound beam forming. Each element may incorporates quarter wave matching layers for better transfer of power. The preferred operating frequency of the RF electrodes may be in the range of 0.5 to 5 MHz with applied energy ranging from 5 to 100 W.

While the invention has been illustrated and described in detail in the drawings and foregoing description, the same is to be considered as illustrative and not restrictive in character. Only certain embodiments have been shown and described, and all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding. Thus, the specifics of this description and the attached drawings should not be interpreted to limit the scope of this invention to the specifics thereof. Rather, the scope of this invention should be evaluated with reference to the claims appended hereto. Finally, all publications, patents, and patent applications cited in this specification are herein incorporated by reference to the extent not inconsistent with the present disclosure as if each were specifically and individually indicated to be incorporated by reference and set forth in its entirety herein.

What is claimed is:

1. A catheter comprising:
   an outer catheter body having a plurality of surface electrodes on a distal portion thereof, the outer catheter body defining a first lumen;
   an inner catheter body containing an ultrasound transducer array adapted to transmit and receive ultrasound waves and positioned within the first lumen of the outer catheter body;
   and an acoustic couplant between the inner and outer catheter bodies so as to provide an acoustic path for ultrasound transmitted and received by the array,
   wherein the array defines an image field and is constructed and arranged to provide ultrasound imaging information of tissue near the surface electrodes; and
   wherein a plurality of the surface electrodes are positioned so as to be in the image field of the array at the same time, and wherein at least two of the electrodes in the image field have substantially different thicknesses such that at least one of the electrodes in the image field is substantially opaque to the ultrasound waves and at least one of the electrodes in the image field is substantially transparent to the ultrasound waves.

2. The catheter of claim 1 wherein the outer catheter body includes at least one proximal connector electrically connected to the surface electrodes via wires embedded in the outer catheter body.

3. The catheter of claim 1 further comprising first and second proximal connectors electrically connected to different ones of the surface electrodes.

4. The catheter of claim 1 wherein the surface electrodes comprise a first plurality of ablation electrodes adapted to ablate cardiac tissue and a second plurality of mapping electrodes adapted to sense intracardiac electrical activity.

5. The catheter of claim 1 wherein the ultrasound array transmits at a characteristic frequency greater than 10 MHz.

6. The catheter of claim 5 wherein the ultrasound array is configured such that it transmits and receives ultrasound through one or more of the surface electrodes, wherein the thickness of the electrode relative to the direction of ultrasound propagation is less than about 5 μm.

7. The catheter of claim 1 wherein a proximal portion of the inner catheter body is coupled to a proximal portion of the outer catheter body so as to prevent relative translation of the inner and outer catheter bodies.

8. The catheter of claim 1 wherein at least the distal portions of the first lumen and the inner catheter body are non-circular in cross section.

9. The catheter of claim 1 wherein the surface electrodes comprise ablation electrodes and the distal portion includes a temperature sensor.

10. The catheter of claim 1 further comprising a steering mechanism coupled to the outer catheter body.

11. The catheter of claim 10 wherein the outer catheter body includes a plurality of steering wire lumens.

12. The catheter of claim 1 wherein the array is a side looking array which operates at a characteristic frequency above 5 MHz.

13. The catheter of claim 12 wherein the array has a distal end and a proximal end and wherein at least one of the surface electrodes is positioned on the outer surface of the outer catheter body longitudinally between the distal and proximal ends of the array.

14. The catheter of claim 13 wherein a plurality of the surface electrodes are positioned between the distal and proximal ends of the array.

15. The catheter of claim 13 wherein a surface electrode positioned between the distal and proximal ends of the array has a thickness less than 5 μm so as to be substantially transparent to ultrasound from the array.

16. The catheter of claim 13 wherein a surface electrode positioned between the distal and proximal ends of the array has a thickness greater than 25 μm so as to be substantially opaque to ultrasound from the array.

* * * * *